US 9,108,050 B2

(12) United States Patent
Bula et al.

(10) Patent No.: US 9,108,050 B2
(45) Date of Patent: Aug. 18, 2015

(54) SYSTEM FOR THE DELIVERY OF PROTON THERAPY BY PENCIL BEAM SCANNING OF A PREDETERMINABLE VOLUME WITHIN A PATIENT

(71) Applicant: PAUL SCHERRER INSTITUT, Villigen Psi (CH)

(72) Inventors: Christian Bula, Lostorf (CH); David Meer, Brugg (CH); Eros Pedroni, Brugg (CH)

(73) Assignee: Paul Scherrer Institut, Villigen/PSI (CH)

( * ) Notice: Subject to any disclaimer, the term of this patent is extended or adjusted under 35 U.S.C. 154(b) by 0 days.

(21) Appl. No.: 14/390,472

(22) PCT Filed: Mar. 28, 2013

(86) PCT No.: PCT/EP2013/056732
§ 371 (c)(1),
(2) Date: Oct. 3, 2014

(87) PCT Pub. No.: WO2013/149945
PCT Pub. Date: Oct. 10, 2013

(65) Prior Publication Data
US 2015/0099917 A1    Apr. 9, 2015

(30) Foreign Application Priority Data
Apr. 3, 2012    (EP) .................................... 12163004

(51) Int. Cl.
*A61N 5/00* (2006.01)
*G21K 1/00* (2006.01)
*A61N 5/10* (2006.01)

(52) U.S. Cl.
CPC ....... *A61N 5/1067* (2013.01); *A61N 2005/1087* (2013.01)

(58) Field of Classification Search
USPC .......... 250/491.1, 492.1, 492.3, 493.1, 505.1, 250/526; 315/501–505, 507, 111.81
See application file for complete search history.

(56) References Cited

U.S. PATENT DOCUMENTS 7,560,715 B2 * 7/2009 Pedroni ....................... 250/492.3
7,838,855 B2   11/2010 Fujii et al.
8,541,762 B2    9/2013 Claereboudt et al.
(Continued)

FOREIGN PATENT DOCUMENTS

EP       2005993 A1    12/2008
WO    2011121037 A1    10/2011

OTHER PUBLICATIONS

Zenklusen S. M. et al; "A study on repainting strategies for treating moderately moving targets with proton pencil beam scanning at the new Gantry 2 at PSI"; Physics in Medicine and Biology.; vol. 55; pp. 5103-5121; ISSN: 0031-9155DOI: 10.1088/0031-9155/55/17/014; XP020196897.

*Primary Examiner* — Bernard E Souw
(74) *Attorney, Agent, or Firm* — Laurence A. Greenberg; Werner H. Stemer; Ralph E. Locher

(57) ABSTRACT

A system and a method improve a quality of beam delivery in proton therapy by pencil beam scanning of a predeterminable volume within a patient that minimizes beam position errors. The system has a proton source generating a proton beam, a number of proton beam bending/focusing units, a beam nozzle having an outlet for the proton beam to penetrate the predetermined volume, a beam bending magnet, and a couple of sweeper magnets to sweep the proton beam in both lateral directions. A position-sensitive detector is aligned with the nozzle to control the position of the proton beam and control logic controls the position and the energy of the proton beam and has a beam steering data set. A correction logic is aligned with the control logic for correcting beam position errors by comparing an expected beam position with the actual beam position detected and generates beam position correction data.

8 Claims, 9 Drawing Sheets

(56) References Cited

U.S. PATENT DOCUMENTS

| | | | |
|---|---|---|---|
| 2007/0029510 A1* | 2/2007 | Hermann et al. | 250/493.1 |
| 2008/0023644 A1* | 1/2008 | Pedroni | 250/400 |
| 2008/0217561 A1* | 9/2008 | Mackie et al. | 250/492.3 |
| 2009/0200481 A1* | 8/2009 | Mackie et al. | 250/396 ML |
| 2009/0212231 A1* | 8/2009 | Hill et al. | 250/396 R |
| 2010/0176309 A1* | 7/2010 | Mackie et al. | 250/492.3 |
| 2011/0105821 A1 | 5/2011 | Dieter et al. | |
| 2013/0068938 A1* | 3/2013 | Heese | 250/252.1 |

* cited by examiner

SYSTEM FOR THE DELIVERY OF PROTON THERAPY BY PENCIL BEAM SCANNING OF A PREDETERMINABLE VOLUME WITHIN A PATIENT

BACKGROUND OF THE INVENTION

Field of the Invention

The present invention relates to a system for the delivery of proton therapy by pencil beam scanning of a predeterminable volume within a patient.

This invention is related to a system for delivering proton therapy (or ion therapy) with pencil beam scanning as it is disclosed in the European Patent Application EP 1 584 353 A1. Due to the finite range of the charged particles and the increasing dose at the end of the proton range giving rise to the so-called Bragg peak, proton therapy permits to deliver more dose into the target volume while sparing surrounding healthy tissues. This is the rationale for using proton therapy for achieving superior results as compared to conventional therapy with photons and electrons.

The most traditional established method for delivering the dose in proton therapy is by scattering. The proton beam is scattered with material in the beam ahead of the patient, such that an uniform proton fluence in the solid angle covering the target is achieved. The dose is shaped laterally with collimators. A spinning wheel of varying thickness modifies the proton range as a function of the time such as to produce a fixed spread-out-Bragg-peak (SOBP). This provides a uniform distribution of the dose in depth. The dose distribution can be further shaped with compensators to coincide with the distal aspect of the target.

An alternative method as disclosed in the European Patent Application EP 1 584 353 A1 is to deliver proton therapy by the pencil beam scanning. The beam is delivered into the patient as the sum of small physical pencil beams. The dose distribution is shaped in the lateral direction by scanning the beam by magnetic deflection using so-called sweeper magnets in the beam line upstream of the patient. The shaping of the dose in depth can be achieved by changing the energy with the beam line, the solution considered in this context. The lateral dose painting is applied with a fixed energy. The procedure is then repeated for several energies. The resulting "energy layers" are delivered with differently shaped lateral proton fluences. In this way the dose distribution can be exactly tailored to coincide with the shape of the target in all three dimensions (three-dimensional dose conformation).

Currently, the pencil beam scanning is considered as a more precise and modern approach to proton therapy than scattering. In fact today it is more or less accepted that scanning is a necessary development in proton therapy for competing with the newest developments in conventional therapy with photons, intensity modulated therapy (IMRT) and tomotherapy. A good example of the superior flexibility of scanning is the development of intensity modulated proton therapy (IMPT) at the Paul Scherrer Institute, CH-5232 Villigen PSI. PSI has pioneered the introduction of pencil beam scanning in the 90's. Reference is made here to the realized Gantry 1 of PSI, which for more than a decade has been the only system in the world treating patients with pencil beam scanning on a gantry.

Today, a need to develop fast scanning methods for coping with the organ motion problems is existing. Of particular relevance for the present invention is the development of new scanning methods, aiming at a very high scanning speed. A certain disadvantage of pencil beam scanning is the high sensitivity of this method to organ motion. If the tumor moves during the delivery of the three-dimensional dose painting, the dose homogeneity within the target can be substantially damaged.

A possible solution to this problem is to use a very fast scanning. With very fast dose painting the interference patterns of the target motion with the motion of the beam can be smeared over a larger target area (volume) and the dose errors get smoothed out. If the target is repainted many times the dose errors are further reduced by statistical averaging.

The need to use very fast energy changes for providing volumetric repainting is therefore present. Fast scanning should be applied not only within a single energy layer but also in depth to provide repainting in range as well (volumetric repainting). This is the reason to aim at very fast energy changes. Scanning systems capable of delivering substantial volumetric repainting are not yet available on the market. Therefore, the present invention particularly aims at scanning systems providing very fast changes of the beam energy applied with the beam line (the beam transport system). The major problem encountered in using a system with fast energy changes of the beam line, is the appearance of systematic errors due to magnetization and eddy current effects affecting dynamically the position of the scanning beam, which spoil the quality of the dose distribution. The observed position errors decay partially as a function of the time and depend strongly on the history and timing of the energy changes.

The Gantry 2 System at the PSI

A unique first gantry prototype capable of delivering proton therapy with very fast energy changes (faster by at least an order of magnitude than all presently known systems worldwide) has been built at PSI for exploring the delivery of highly volumetric repainted pencil beam scanning. This system is being commissioned now at the respective PSI institute.

There, the development of a fast volumetric scanning has been started, because this method is possibly of crucial importance for delivering the proton dose using pencil beam scanning also for moving tumors, like for lung and liver cancers and other targets in the trunk and abdomen. Up to now scanning beams have been applied only to static tumors.

Technical Specifications of the Scanning System of Gantry 2

The scanning speed in the lateral direction corresponds to 0.5 cm/ms in the U direction (dispersive plane of the gantry beam line) and 2 cm/ms in the T direction (transverse). For this purpose, two (U and T) sweeper magnets are placed before the last 90° bending of the beam line in direction to the patient. The energy changes are performed with a degrader and by changing the settings of the whole beam line which brings the beam from the accelerator to the patient through the gantry in the corresponding treatment area.

The proton range can be changed for a typical step size of 5 mm in water within 80 milliseconds, which is in its kind a world record. The experience of using such a system is therefore unique. The beam stability problems observed with Gantry 2 and described in this application have not been reported in the literature beforehand and are probably not yet known by experience outside of the PSI team (but that problems with eddy currents and magnetization effects would have been found at this high scanning speed is not a surprise). The Gantry 2 system supports also the use of the dynamic modulation of the beam intensity at the time scale of 100 microseconds (deflector plate after the ion source of the cyclotron). This feature is of some relevance for providing a good reproducibility of the timing characteristics of the scan sequences.

Beam Tuning

The beam energy is usually changed with the beam switched off. The energy changes are applied simultaneously to all elements of the beam line. The electric current values of the power supplies of the various beam line magnets are send in a single command from the control system of scan (therapy control system—TCS) to the machine control system of the whole facility (machine control system—MCS). The data are derived from pre-calculated data tables (beam tunes data files). All magnetic elements of the beam line (dipoles and quadrupoles) are laminated to adapt very quickly to the new settings of the new nominal beam energy. Changing the setting of mechanical devices (except the degrader which is fast) is avoided in order to achieve a very high speed. When the beam line is ready, it sends back a ready signal to the TCS and the proton beam can be switched on again and used.

When applying the settings of a tune file, the beam is expected to be received at the right position at any instance. The beam tune files are "frozen data", which are supposed to be used without any modification (i.e. without applying any re-tuning of the beam line).

When working with very rapid changes of the beam energy one is at some point inevitably faced with errors in position and range of the pencil beams, which are due to uncontrolled magnetization and eddy currents effects in the bending magnets of the beam line. The experience with the prototype of Gantry 2 has shown that a very fast scanning approach is feasible in principle, but that it suffers in practice from relevant systematic errors of the beam position produced by beam drifts up to 3 mm, which are medically not acceptable. These errors are due to dynamic magnetization and eddy current effects in the magnets. They represent a last major problem for achieving a very high scanning speed.

The PSI team has learned with the Gantry 2 prototype that these errors are very difficult to predict and to model. The present experience indicates however, that the magnetization errors are astonishingly well reproduced, when the given scan sequence is exactly repeated (reproducible behavior of the dose fields).

BRIEF SUMMARY OF THE INVENTION

It is therefore an objective of the present invention to provide a system and a method for improving the quality of beam delivery in a system for proton therapy by pencil beam scanning of a predeterminable volume within a patient that minimizes the extent of possible beam position errors to an extent medically acceptable.

This objective is achieved according to the present invention by the features given in the independent claims. Preferred embodiments of the present invention are given in the dependent claims.

With respect to the system, this objective is achieved according to the present invention by a system for the delivery of proton therapy by pencil beam scanning of a predetermined volume within a patient, comprising:
a) a proton source in order to generate a proton beam being adjustable with respect to the beam intensity and/or beam energy, i.e. by means of a degrader;
b) a number of proton beam bending and/or focusing units;
c) a beam nozzle having an outlet for the proton beam to penetrate the predetermined volume of the patient;
d) a beam bending magnet being disposed upstream of the nozzle;
e) a couple of sweeper magnets in order to sweep the proton beam in both lateral directions;
f) a position-sensitive detector being aligned with the nozzle in order to control the position of the proton beam; and
g) a control logic for controlling the position and the energy of the proton beam comprising a beam steering data set;
h) a correction logic aligned with the control logic for correcting beam position errors by comparing an expected beam position with the actual beam position detected in the position-sensitive detector and generating beam position correction data in dependency of the comparison results.

With respect to the method these objectives are achieved according to the invention by a method for improving the quality of beam delivery in a system for the delivery of proton therapy by pencil beam scanning of a predetermined volume within a patient, comprising the steps of:
a) providing a proton source in order to generate a proton beam being adjustable with respect to the beam intensity and/or beam energy, i.e. by means of a degrader;
b) providing a number of proton beam bending and/or focusing units in order to generate a beam line;
c) providing a beam nozzle (1) having an outlet for the proton beam to penetrate the predetermined volume of the patient;
d) providing a beam bending magnet being disposed upstream of the nozzle;
e) providing a couple of sweeper magnets in order to sweep the proton beam in both lateral directions;
f) providing a position-sensitive detector being aligned with the nozzle in order to control the position of the proton beam; and
g) providing a control logic for controlling the position and the energy of the proton beam by using a beam steering data set;
h) providing a correction logic aligned with the control logic for correcting beam position errors by comparing an expected beam position with the actual beam position detected in the position-sensitive detector and generating beam position correction data in dependency of the comparison results.

The present invention therefore offers advantageously various options for the type of corrections which are in detail explained below. Preferably, a combination of a more generic correction mechanism and a more patient related correction mechanism which might be enriched by a self-teaching mechanism is often chosen. The present invention therefore achieves the highest inherent precision of the scan, without having a final precise knowledge on how the system reacts in all circumstances. Therefore, the system and the method cope with limiting systematic effects, like eddy currents and magnetization errors in the magnets of the beam line. In particular, the use of the self-teaching of the beam delivery copes with remnant errors, which are reproduced but extremely difficult to predict. The goal of increasing the flexibility of the system and the method for working with essentially any scan delivery pattern has been achieved.

For the benefit of a direct improvement on the position preciseness, the beam position correction data can be introduced into the beam steering data set, preferably automatically introduced after running a therapy-independent test irradiation data set. This feature therefore enables to realize a generic dynamic correction data set which can be incorporated into each steering data set.

When in the therapy-independent test irradiation data set all significant change in beam position and beam energy variations and/or rampings are comprised, then the opportunity arises to provide different generic dynamic correction data sets which are established in form of functions depending on the energy change and/or the gradient of the energy change and/or the intended beam position and/or the history of the beam delivery.

As seen from the experimental results, the correction logic may use a first correction model for correcting beam position errors which decays as a function of the time after a change of the proton energy occurred.

The self-learning approach of the system and the method can be achieved when the correction logic comprises an automated software for feeding back the beam position correction data derived from the comparison data logged from a patient-specific test irradiation for the verification of an patient-specific beam steering data set into an improved new version of the beam steering data set of the patient-specific irradiation which is then qualified to be used for treating the patient in at least one, preferably all, subsequent irradiations.

In order to further improve the preciseness of the beam position fidelity, a second position sensitive detector can be integrated into a patient table which preferably is disposed in the iso-center of the proton beam geometrics.

Preferred embodiments of the present invention are explained in more detail with respect to the attached drawings which depicts in:

DESCRIPTION OF THE INVENTION

Figure 1:
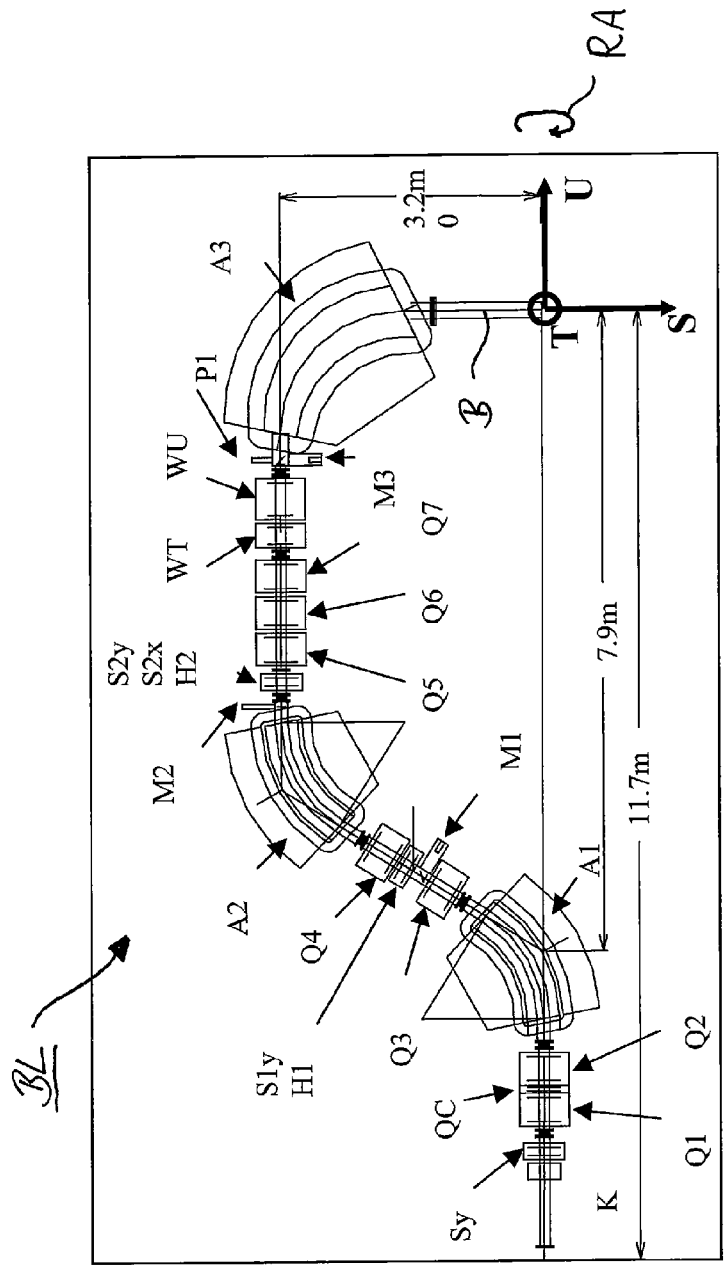
FIG. 1 a schematic view on the key components of a beam delivery line.
Figure 2:
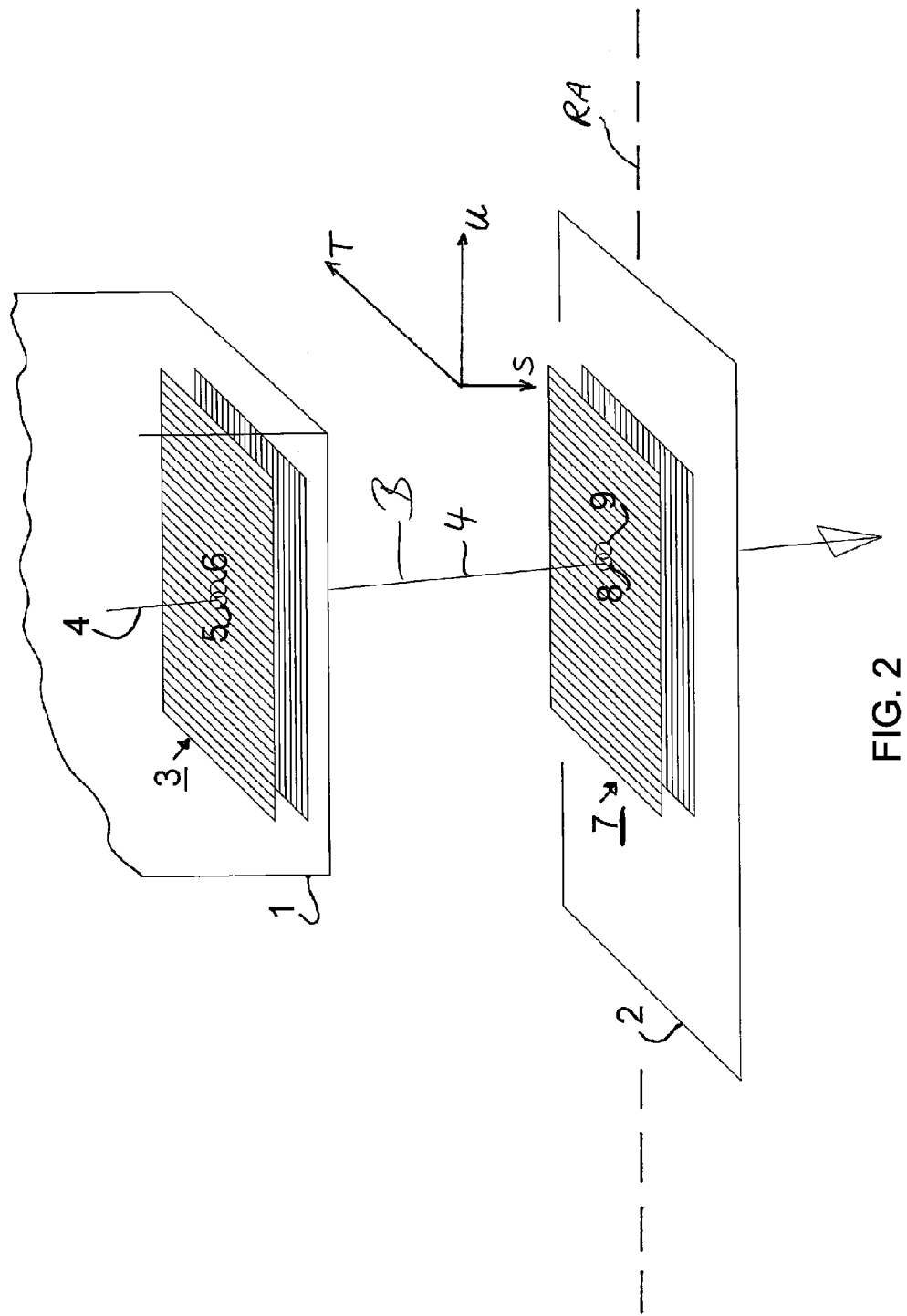
FIG. 2 a schematic view on the relation of the beam position measured at the nozzle to the position of the beam in the tumor at the iso-center.

For the purpose to illustrate the proton beam delivery components, a so-called beam line BL used for the application of the proton beam B to the target volume within a patient is schematically shown in FIG. 1 wherein FIG. 2 shows in addition to FIG. 1 components required with the present invention. This beam line BL comprises a system of three dipoles A1, A2, A3 and seven quadrupols Q1 to Q7. Other elements are steering magnets Sx/y (some of those elements are embedded as separate windings in the sextupoles H), optional slits or fixed collimators K, beam diagnostic elements M and vacuum pumps P. The main dynamic elements for the scanning are the two sweeper magnets WU and WT and a dynamic quadrupole corrector QC.

The beam optics calculations were performed for a nominal beam energy of 230 MeV (other energies are obtained by scaling the electric current in the magnetic elements of the beam line BL according to the momentum of the beam B). The bending radius applied to the beam B is chosen to 1.5 m. The nominal field is B=1.5 Tesla. The radial parallel displacement of the beam line BL from the rotation axis RA is about 3.2 m. The distance of the exit field boundary of the 90° bending magnet A3 to the iso-center (where the beam B hits the rotational axis RA of the beam line BL—also termed Gantry) is approx. 1.7 m. This space available in this embodiment is sufficient for keeping the bulk of the 90° bending magnet A3 during rotation to stay outside of a not shown treatment room at a distance of about 1.2 m from the iso-center, in order to keep the ceiling of the treatment room at least 2.4 m high (normal room height) which is a significant improvement for the mental well-being of the patient. The shape of the beam line BL is derived from these settings, by using the minimal space necessary to place all beam transport elements needed to fulfill the beam optics requirements inside the most minimal space of a support frame. This beam line BL offers therefore the full parallelism of the beam B during painting, a true size imaging from the starting point of the rotating beam line (gantry coupling point) to the iso-center (the end point where the beam B is scanned in the patient). Further, beam achromatism and beam focus invariance during double sweeping in U- and T-direction is achieved.

The beam delivery elements disposed upstream of the beam line BL are not shown. A cyclotron delivers a continuous beam being adjustable with respect to its energy and intensity. The change of the energy will be preferentially done by changing dynamically the setting of a degrader and the tune in the beam line BL ahead. Between the cyclotron and the degrader a fast kicker magnet is mounted for the switching ON and OFF of the proton beam with a reaction time of only 50 µs.

Hereinafter the main devices are presented, which are used for coping with the problems discussed above. In FIG. 2 now only the elements are drawn, whose functionality is related to the control of the position of the scanned beam during treatment delivery and are therefore of relevance for the present invention. The generic design of a proton beam gantry is, for example, shown in FIGS. 2 and 3 of the European Patent Application EP 1 584 353 A1.

Individual proton beams 4 are delivered during scanning by the beam line under the action of the control system (TDS). The addition of very many pencil beams each of different intensity, position and energy results in individually conformed dose distributions. This is the basic idea of a treatment by pencil beam scanning. The basic mode considered in the following is a step-and-shoot-method, where the beam is switched off when it is being moved to the next spot position (discrete spot scanning).

The last part of the beam line is ending in the so called nozzle 1 which is the enclosure of the equipment for monitoring the beam before it reaches the patient. Within the nozzle 1 several devices are incorporated which are used to control and check the proper functioning of the beam delivery system during treatment.

A position sensitive detector 3 is incorporated into the nozzle 1. The scope of this detector 3 is to check the position of the pencil beam during scanning. On Gantry 2 of the PSI, a strip ionization chamber 3 is used with 2 mm wide strips permanently mounted in the nozzle 1. This detector measures at the end of a beam spot the effective position 5 and width of the beam 4. The detector 3 collects the ionization of the gas in the chamber in the T and U strips.

The trace of the beam 4 appears as U- and T-projected profiles. From the profiles, the mean value (position) and standard deviation (beam width) is extracted. These values must match with prescribed expected values 6, which are stored in a so-called verification file. The verification checks are done in a separate computer (therapy verification system—TVS). If the beam is not at the proper location within the predetermined tolerance an interlock has been produced in the installations so far known in the prior art.

The position sensitive detector 3 measures on-line the position of the scanned beam 4 on a spot by spot basis. The tests are performed at the end of a spot delivery after waiting for about one millisecond for the termination of the collection of the ionization charge on the strips. For highly weighted spots the achieved precision of measuring the beam position is of the order of a few tens of a millimeter. The precision diminishes if the spots are very short.

The difference between measured and expected beam position must agree within typically 1 to 1.5 mm, otherwise the scan sequence will be interrupted by an interlock. The beam position checks during treatment delivery represent a major safety requirement of the scanning system, to make sure that the beam is being properly delivered in both lateral directions of the scan.

A patient table 2 is positioned such that the tumor (the volume to be treated) is located at the iso-center. With a rotating gantry the iso-center is usually the location where the beam axis exiting the nozzle 1 crosses the rotation axis RA of the gantry (see also FIGS. 2 and 3 of the European Patent Application EP 1 584 353 A1).

To the scope of calibrating the beam delivery system, a second position sensitive monitor 7 can be placed optionally on the patient table 2. This element is used only for commissioning the beam delivery system or for performing quality assurance checks. With both strip chambers in place the relation of the beam position measured in the nozzle 1 with the actual beam position at the iso-center can be measured. During patient treatment the second strip chamber 7 is here not available. However, a second detector could be present on the patient table 2 or directly on the patient.

In the present system an established relation of the beam position in the nozzle 1 to the one within the patient body is existing. A peculiarity of the Gantry 2 system is that beam optics of the system has been designed to provide a parallel scanning in both T and U scanning directions. The measured data of the detector 3 in the nozzle 1 and the detector 7 at the iso-center should be to first order identical. In practice, a parameterization of the beam directions as a function of the U and T coordinate of the scan (for different energies and gantry angles) is provided. Look-up tables describe the projection of the scanned beam backwards from the iso-center to the nozzle 1 (nozzle back-projection). An essential prerequisite for the safety function executed by the position sensitive detector 3 in the nozzle 1 is the certainty that the beam back-projection (relation between beam position at the tumor location and at the detector in the nozzle) is known and stable at any time. The stability of this relation is verified on a daily basis prior to starting patient treatments and is known to be constant over years.

The safety function is based on the knowledge that a faulty situation producing a change of the beam direction without affecting at the same time the beam position in the nozzle 1 is extremely unlikely to happen.

Another safety feature for a pencil scanning system is the requirement to record all relevant data of the scan in so-called log-files. These files document and store all the measured parameters of a given fraction. They contain also the measured and expected beam spot position data in the nozzle 1. These data are in principle available for learning how to improve the precision of the beam delivery Gantry 2 of PSI is capable of controlling dynamically the beam intensity at the accelerator source with a rather high precision. Instantaneous dose rates can be set from within the steering file of the scan for each energy tune and in-between. This helps to obtain a very good reproducibility of the scan sequence timing for each specific file, which in turn allows to provide reproducible dynamic corrections to the system.

Presently, a controlling of the beam position is achieved with so-called "static" tune files. The values provided in the tune files are static, in the sense that the characteristics of the beam (for the central beam without lateral scan) have been measured after applying the energy changes slowly—with a long pause of many seconds before switching the beam on again after the energy changes (beam centering commissioning with "static measurements"). These static corrections have been implemented as energy and gantry angle dependent corrections embedded in the beam tune files. The corrections are activated in the tune data generation process (tune files generation).

Even with such a prior knowledge of the system obtained from basic commissioning data, the operator of the beam line is still faced with dynamic position errors of the beam delivery of up to 3 mm when the system is used with scanning in a fast dynamic mode.

Proper Energy Ramping

One option to improve the performance of using dynamic scans is to restrict the use of the system to a fixed way of scanning the energy. With this basic mode (full ramping) the beam energy is scanned from the nominal maximum to the nominal minimum in sequence completely up-down and down-up. The energy steps are distributed in series along a measured hysteresis energy curve without change of direction. With a proper ramping the errors becomes quite acceptable (<1 mm), but only for the small energy steps at the interior of the SOBP. The first big energy jump from the maximum energy down to the first value of the SOBP can produce dynamic position errors up to 3 mm (this maximal error arises when the step is over the full energy range).

It has been further observed that the remnant position errors due to the dynamics of the scan have their maximum value immediately after an energy change and that they decay as a function of the time with a time constant of the order of a couple of seconds which is now also reflected in a preferred embodiment of the present invention.

The present invention now introduces two additional sets of corrections (steps) in the production of the steering files for better controlling the dynamic effects due to eddy currents and magnetization. The errors are more pronounced in the U direction (which is on the bending plane of the beam line of the gantry).

In the first step generic dynamic corrections are applied which model the dynamic position corrections decaying as a function of the time. The experimental observations have shown that a rather complex modeling of the beam position dynamics is needed. A first set of generic corrections has been introduced assuming that the system is running with proper ramping. Pre-calculated beam position corrections are applied as offsets to the steering data of the sweeper magnets WT, WU. The initial amplitude of the correction is modeled as a function of the end energy and of the energy step lastly applied. The correction is calculated with an exponential decay as a function of the time elapsed since the last energy change. The decay time constant depends on the beam energy. Presently, different sets for the up-down and down-up direction are existing. The corrections are applied as cumulative contributions, in the sense that the amplitude for a new energy step is added to the decayed value of the previous step. The cumulated amplitude then decays as a function of the time with an averaged time constant of the previous and current step. This approach is termed the generic model of the cumulated dynamic beam position errors.

With this approach the precision of the beam delivery can be improved by a significant factor (from 2 to 5). The results are quite close to be acceptable but still not completely satisfactory. And they are applicable only if a proper ramping is used.

The use of this step is not known in the literature and is not state of the art in proton therapy yet. After using this step remnant systematic errors have still been observed related to the individual history of each scan (depending on the steps sequence, time intervals and amplitudes of the energy changes). Eddy current effects seem to have an influence on the system beyond individual steps. Magnetization effects seem also to depend on the detailed history of the previous energy steps. It has been further observed that changing the scanning direction within a ramping loop produces the largest dynamic position errors. It was observed that the dynamic position errors in the nozzle and at the tumor location at the iso-center are always extremely well correlated (see FIG. 8).

In the second step of the present example the goal has then been to further reduce the dynamic effects by using scan-specific corrections derived from the logged data of a test run. The second step provides for scan specific corrections and a "Self teaching" of the beam delivery system using the logged data of a test run of an individual therapy-related irradiation plan (patient-field specific steering file) for the dose distribution to be achieved.

The logged data of a previous run has been used for correcting the yet uncontrolled but reproducible position errors due to the high dynamics of the scan. The new solution comprises running the system with a patient-field specific steering file a first time—without or with patient (in a test run or for a first not corrected fraction followed by typically 20 to 30 corrected fractions). The beam position during the scan is measured with the beam position sensitive detector 3 in the nozzle 1 in front of the patient. The logged data are analyzed off-line and the resulting position errors are implemented as individual beam spot corrections into a new (corrected) steering file. In this way the system measures and corrects itself to the limits given by the precision of the measurements, i.e. "the system teaches itself". The so-established corrections are patient and field-specific and are applied advantageously without further modifications to all subsequent irradiations (fractions). This approach (self-teaching beam delivery) results in a remarkably improved precision of the beam delivery.

In a preferred embodiment of the present invention, both, the generic dynamic corrections (with time decay) and the scan specific corrections, are used in order to limit the size of the scan specific corrections and thus facilitate recovering from inadvertent situations when the beam delivery is stopped in an unplanned manner, as in the case of interlocks.

Figure 5:
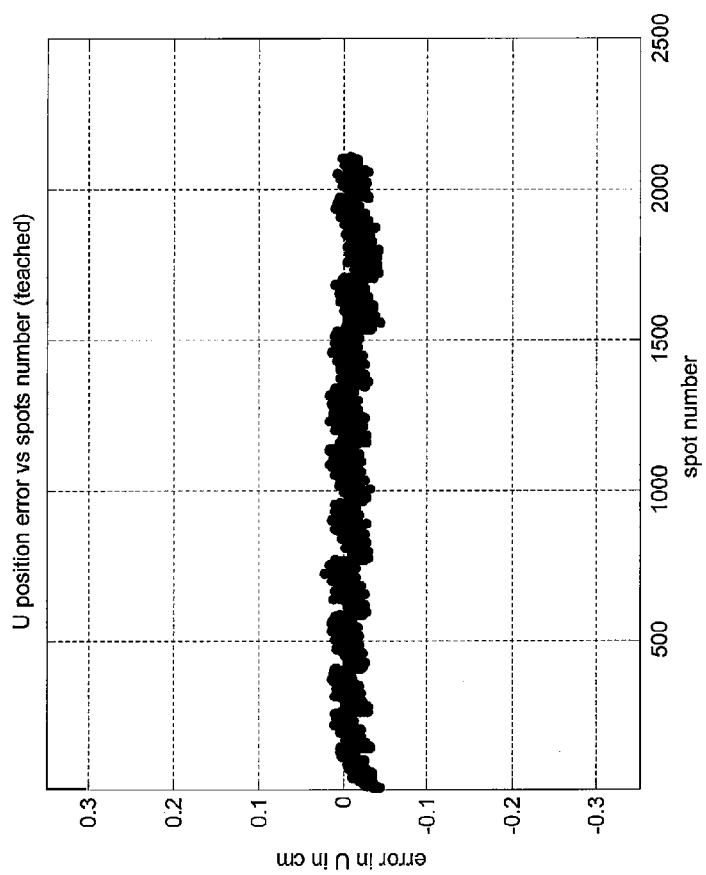
FIG. 5 a scan as shown in FIG. 3 but the scan was performed with generic and scan specific corrections.
Figure 7:
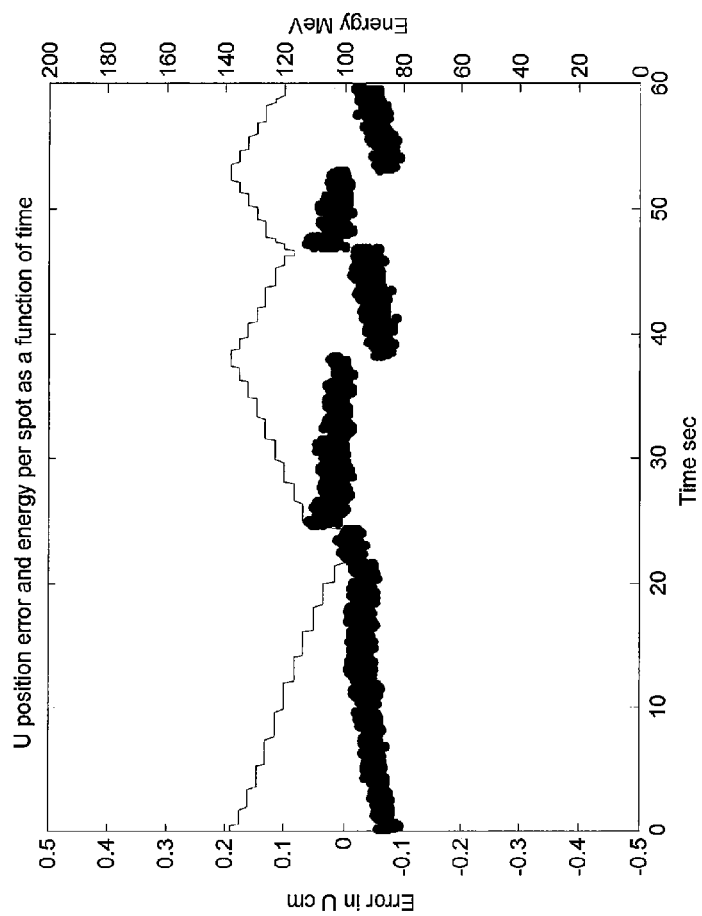
FIG. 7 a scan as shown in FIG. 6 but with scan specific corrections.
Figure 8:
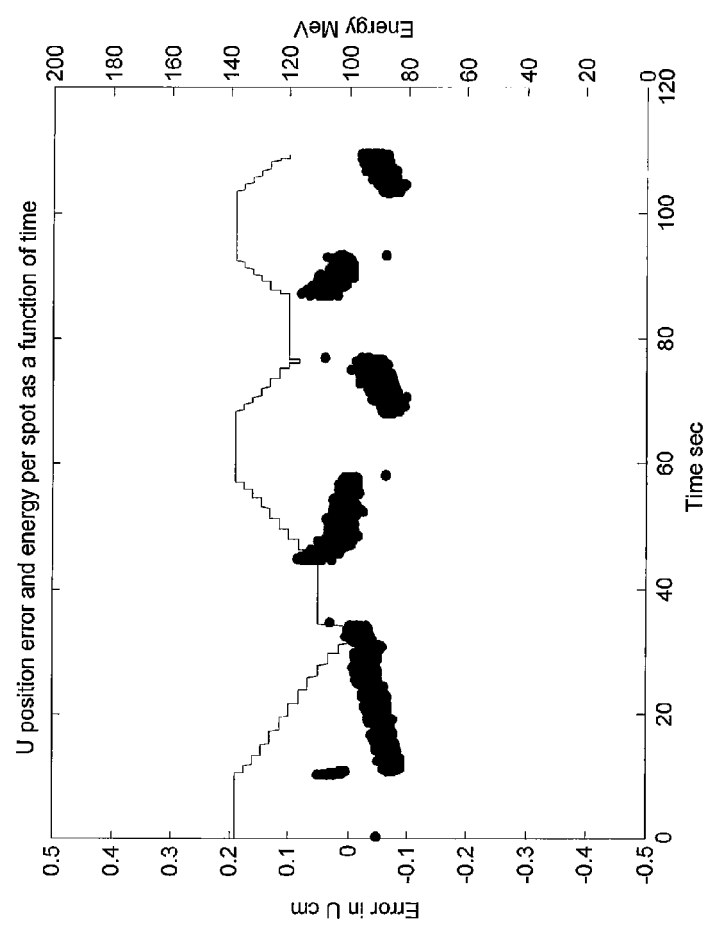
FIG. 8 a scan as shown in FIG. 7 but with 5 times an extra pause of 10 seconds after the first spot following a change of direction of the scan energy (up-down <-> down-up)

The self-teaching mechanism obtained with a test run provides a set of spot by spot position corrections which are embedded in a new version of the steering file. This second step brings the final precision for all subsequent scans down to typically a few tens of 1 mm, as shown in the examples below (FIGS. 5, 7, and 8).

The potential advantages of the invention are manifold. The major achievement of this invention is that it allows using a very fast scanning system, applied with maximum flexibility, while still achieving a very high precision of the scan (with precision close to the resolution of the position measurements using corrections obtained off-line). The spot position errors due to scan-specific magnetization, hysteresis and eddy current effects disappear. The system and the method work in all situations independently of the shape and size of the target volume. The use of the generic dynamic corrections as the basis for self-teaching should have a beneficial effect for restarting the scan in case of treatment interruptions.

The "self-teaching method" reduces the position errors due to the energy dynamics not only with a proper ramping, but also with rather arbitrary energy scan patterns. This advantageously contributes to a reduction of the treatment time of the scan. By increasing the flexibility of the scan a larger variety of repainting strategies can be employed for solving the organ motion problem in the most optimal way. An example of applying self-teaching to a case without proper ramping in shown in the FIGS. 6, 7 and 8.

The concept to use the strip detectors 3 for "guiding the beam" can be used in addition for correcting other small systematic errors. The self-teaching mechanism corrects automatically small calibration errors in the action maps of the scanning magnets. Similarly, beam position errors related to imprecise beam tune commissioning as well as beam position effects due to different gantry angles are also corrected. The only important issue is to maintain a precise knowledge of the back-projection of the beam 4 into the nozzle 1.

That a higher precision is achieved in the subsequent fractions can be proven by analyzing and comparing the log-files before and after correcting the system. The increased precision should permit the use of more stringent tolerances for the position checks on-line during patient irradiations (closing the tolerance window down to less than 1 to 0.5 mm). The corrections can be analyzed off-line before applying the corrected steering file to a patient. One can apply consistency checks to the corrections for assessing their validity. Corrections for very short spots could be dropped for example, if they are found to be too imprecise.

Currently, on Gantry 2 new very advanced beam delivery techniques have been developed with continuous dose painting along lines and target contours, with variable scan speed and with dynamic control of the intensity of the beam. The self-teaching approach is also expanded to be used for correcting the systematic errors of these new continuous scan modes (i.e. to correct the errors due to the dynamic response of the sweeper magnets and of the beam intensity control with a continuously moving scan beam).

Another possibility related to this invention shall be mentioned which is the use of a multi-layer-ionization-chambers (MLIC) placed on the patient table at the iso-center. This instrument is used for the daily checks of Gantry 2, for certifying the correctness of the proton range of the energy tunes. This instrument is used for "teaching" the beam delivery system also in range (range-positional teaching). In practice, the range errors were found to be below 1 mm and are therefore rather small but this approach could be also used in practice in order to increase the preciseness of the dose delivery to the relevant volume within the patient, such as a tumor or the like.

As already mentioned above with respect to the position sensitive detector 7 place in the patient table, there is a more direct possibility for position teaching the system, namely with a monitor positioned directly at the iso-center.

Its use implies however the effort to mount such a monitor on the patient table 2 for each new scan file but the pay-back results may justify this effort.

The use of these new methods provides a "short-cut" of the necessary commissioning work. With this approach it is not necessary to commission the system in all details down to the ultimate precision. Rough preliminary commissioning results can be used immediately for patient treatments, using the system in self-teaching mode. The self-teaching mechanism will take care of delivering the dose with a very good precision from the first patient onwards. This strategy will allow an earlier start of the operation of a new gantry and could relax the financial budget constraints for the most critical phase of a new commercial facility, which is the start-up phase.

From the medical point of view new advanced and fast beam scanning methods are needed for treating moving targets. The self-teaching method according to the present invention is a powerful tool for approaching this goal quickly while maintaining a very good precision. The extension of the medical indications treated with scanning to include moving targets could trigger a total replacement of the established scattering foils technique with solutions based solely on scanning. This could have a remarkable impact on the market of proton therapy.

A very important safety requirement of proton therapy with scanning beams is to check that steering files produced by the treatment planning system and used for guiding the scanned beam during beam delivery are giving the correct dose. A scan shall be thus delivered at least once on the treatment machine without patient (so-called "dry run").

This is especially true at the beginning of the lifetime of a new facility. This task is usually done in combination with verification dosimetry, where the dose field is delivered on a dosimetric phantom. The dose verification system checks that the three-dimensionally shaped dose distribution is correct in magnitude and in shape. With only one additional run the teaching corrections can be provided and it can be verified in a second dosimetric run that the teaching corrections are indeed producing improvements in the dose distribution. The actual patient irradiations are usually applied in typically 20 to 30 fractions at one fraction per day. The dry run and verification runs are usually done outside of the treatment hours and represent therefore a small addition to the total time budget of the system. In addition there is also the possibility to use the 1st fraction of a treatment as the teaching run.

The currently preferred quality assurance procedure (QA) is to place a second identical beam position detector 7 at the iso-center and to save the data of both detectors (at the iso-center and in the nozzle) in the same log-file. It can then be proved that the position corrections derived from the errors in the nozzle 1 are indeed correcting the beam position at the iso-center. This is shown with selected experimental results below. That the improved precision of the beam in the nozzle results also in an improved precision for the dose distribution, this can be proven with verification dosimetry methods.

The self-teaching approach according to the present invention is of practical importance (if not essential) for being able to deliver the dose with very high scanning speed, with high dynamics and to the best precision. This issue is of importance for the growing market of beam delivery systems for proton and ion therapy. The overall increased precision of the scan has a positive effect on the reliability and availability of the system.

The most natural alternative to the self-teaching mechanism would be to use a feed-back loop on-line for correcting the beam position dynamically during beam delivery. This approach is not as easy to implement, because the information on the beam position on-line is based on a rather complex software (if one wants to achieve the highest precision). The use of feed-back loops in the context of the beam delivery has been mentioned at conferences, for solving stability problems of the slow extraction of the beam from synchrotrons on a time scale of seconds (but not for solving problems related to systematic reproducible effects at a very high scanning speed in the range of milliseconds).

Presently, the invention uses a different approach as compared to a feed-back loop on-line for the following reasons: A feed-back loop is limited in practice by the inherent reaction time (loop time) of the measuring system and of the actuators of the loop. The corrections work on a time scale longer than the response time of the loop, which for a strip monitor is at least of the order of several milliseconds. The systematic errors discussed in this application have their maximal effect immediately after an energy change. In the first milliseconds after an energy change, the beam will be inevitably delivered at the wrong position. This error will then be repeated in the same way for all subsequent fractions. The risk to produce interlocks at the energy changes is probably larger with a feed-back then with a self-teaching system.

With the present self-teaching approach the ionization charges deposited on the strips are integrated over the full length of the spot. The information of the dose profile is thus taken with the maximum available precision of the measurements off-line. The precision depends on the given spot time length (the longer the spot, the more precise the correction). A feed-back loop is a good solution for adapting the system to statistical fluctuations. Systematic effects are better analyzed in more details off-line.

Therefore, the self teaching approach is the best way to achieve the best possible precision for a system with high scanning dynamics. The solution is realized by software off-line in the context of the generation of the steering files. The approach is not too difficult to implement. The corrections derived from the self-teaching mechanism are fixed (they work like other modeled predictive correction). Their validity can be demonstrated on-line through the use of quality checks by placing a second strip chamber 7 at the iso-center.

FIGS. 1 and 2 show the basic principles of the system and of the invention.

The strip detector 3 in the nozzle 1 records the position 5 and the width of the impinging proton beam 4 during beam delivery by calculating the mean and standard deviation of the beam profiles projected onto the two orthogonal axis of the chamber (the U and T profiles). With an improper functioning of the system the proton pencil beam appears at a slightly wrong position 5 as compared to the expected position 6. The difference between expected position 6 and measured position 5 are used on line for interrupting the treatment if this difference becomes too big (interlock).

An implicit prerequisite of this test is the precise knowledge of the relation of the nominal beam position in the nozzle 1 to the nominal position 9 of the beam at the iso-center. This relation can be gained by placing a detector, e.g. a second strip detector 7 on the patient table 2 at the iso-center. This optional detector 7 is used for providing the basic projections 8 of the beam from the iso-center into the nozzle 1 (to know in the steering the expected position of the beam 4 in the nozzle 1 in order to position very precisely the beam at the iso-center). That the errors in position at the nozzle (difference 6-5) and the iso-center (difference 9-8) are well correlated in practice is shown from the experimental figures below.

Once a precise relation between nozzle and iso-center has been established (for different beam energies and gantry angles), the position of the beam in the nozzle can be used not only to check but also to guide the proton pencil beam. The other pictures are presented in the section below.

As an example some experimental results are presented, obtained by irradiating a target volume shaped as a sphere of 8 cm diameter. The center of the sphere is located at a depth of 10 cm in water. The scan is performed by moving the beam over a grid with a 5 mm spacing. The grid points (spots) which are at the interior of the sphere are delivered. The intensity of the spots is chosen to achieve a conformal homogeneous dose distribution within the target.

The SOBP has been scanned with 15 energy steps (the range is from about 92 to 138 MeV). The experimental results are displayed as position errors (Difference measured—expected) measured with the second position-sensitive detector 7, here a strip chamber, placed at the iso-center on the patient table 2.

Figure 3:
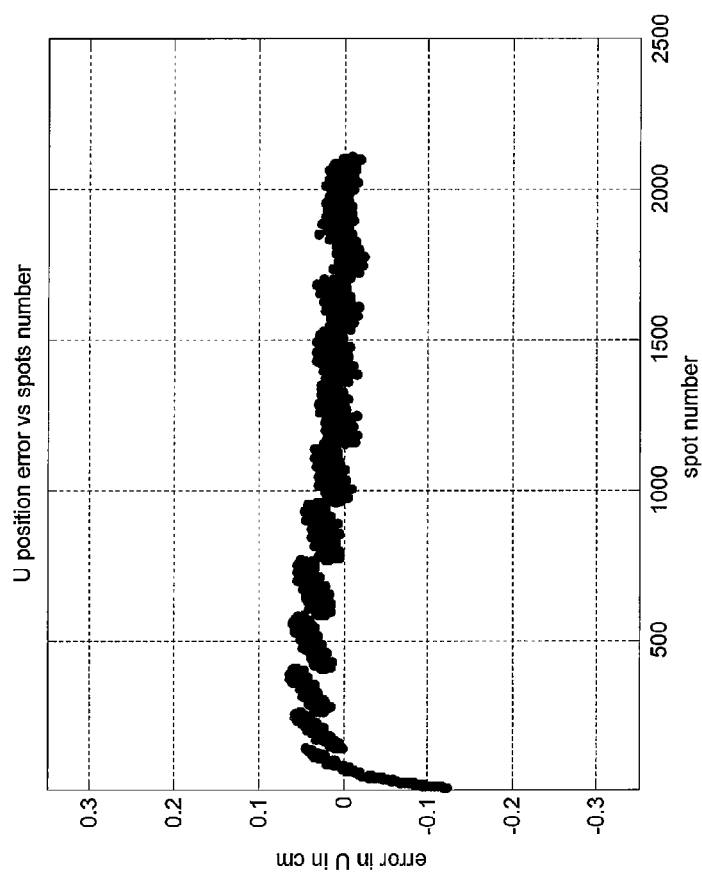
FIG. 3 a scan of a sphere of 8 cm diameter—single painted—with proper energy ramping; the position errors are plotted at the iso-center in the U direction plot as a function of spot number wherein the scan was performed without generic and without scan specific corrections.

FIG. 3 shows the position errors plotted as a function of the spot number. Here a single scan (scan without repainting) has been delivered but applied with proper ramping: first the case without generic and without scan-specific corrections is considered, the issues described in this application. One can easily recognize the exponential decay of the position drifts. The most prominent error is at the beginning of the scan, after the first big energy step from 230 MeV down to 138 MeV.

Figure 4:
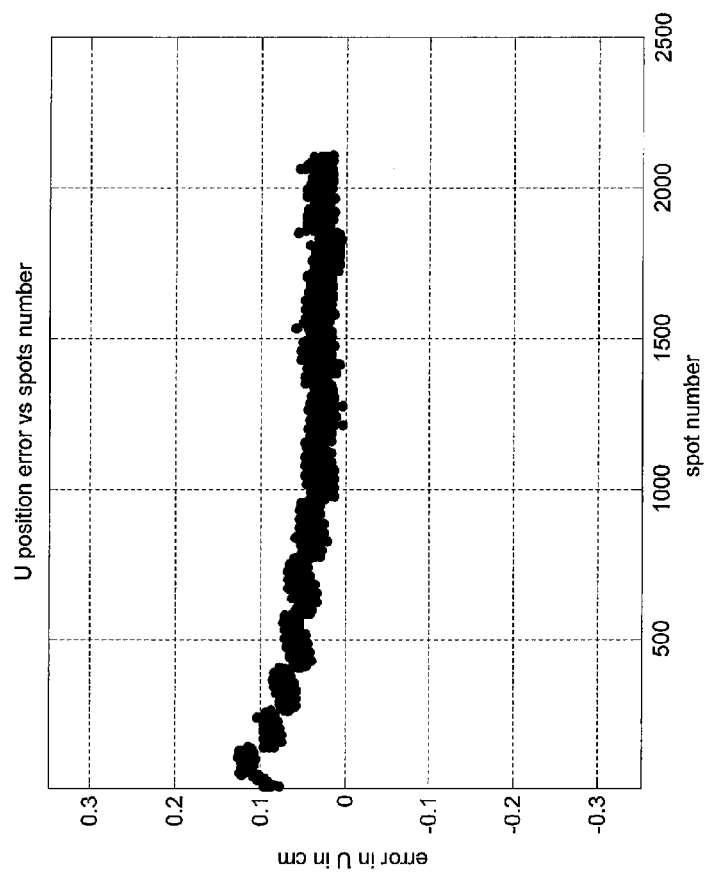
FIG. 4 a scan as shown in FIG. 3 but the scan was performed with generic but without scan specific corrections.

FIG. 4 shows the effect of applying the generic corrections to the same situation as described in FIG. 2. One can see that the exponential behavior is rather well canceled by the generic corrections.

FIG. 5 shows the effect of adding now the self-teaching approach to the case of FIG. 3. The error band is reduced to be within a few tens of a millimeter, quite an astonishing result if one consider that this happens on a beam line which has a length of about 50 meters.

Figure 6:
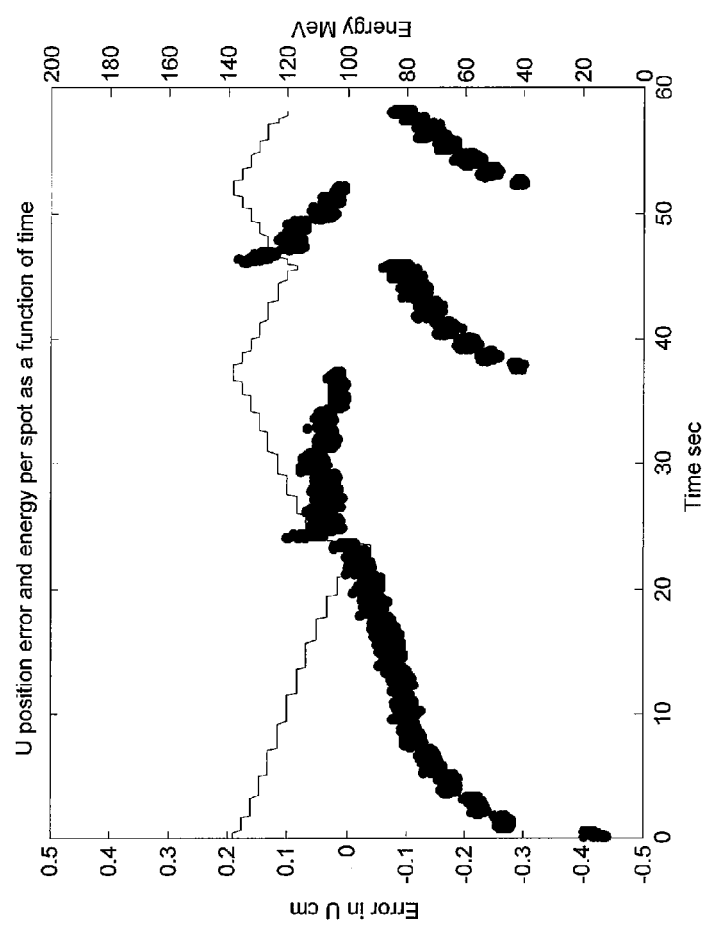
FIG. 6 a scan of a sphere of 8 cm diameter; Iso-layer repainted 5 times without proper ramping; U-position errors at the iso-center and beam spot nominal energy are plotted as a function of the time, the scan was performed with generic but without scan specific corrections.

FIG. 6 shows the case of applying repainting 5 times using the so-called iso-layer repainting method. The iso-layer concept is based on the idea to revisit spots with low weights less often than the most distal spots of the scan.

The ramping at the start of the irradiation has also been intentionally mistaken. During repainting, the direction of stepping the beam energy has been changed without considering any restriction (the steps are not kept along the nominal hysteresis curve). The intention was to produce a rather "wild case" of stepping the energy in order to provoke very large position errors.

FIG. 7 shows the effect of the self-teaching method applied to the case of FIG. 5. The self-teaching approach is capable of reducing the systematic errors of the "wild case" below ±1 mm.

FIG. 8 is identical to FIG. 7, the only difference being the addition of pauses in the steering file to simulate not planned treatment interruptions. By using self-teaching on top of the generic corrections the system reacts quite diligently to treatment pauses also for the "wild case" depicted here.

Figure 9:
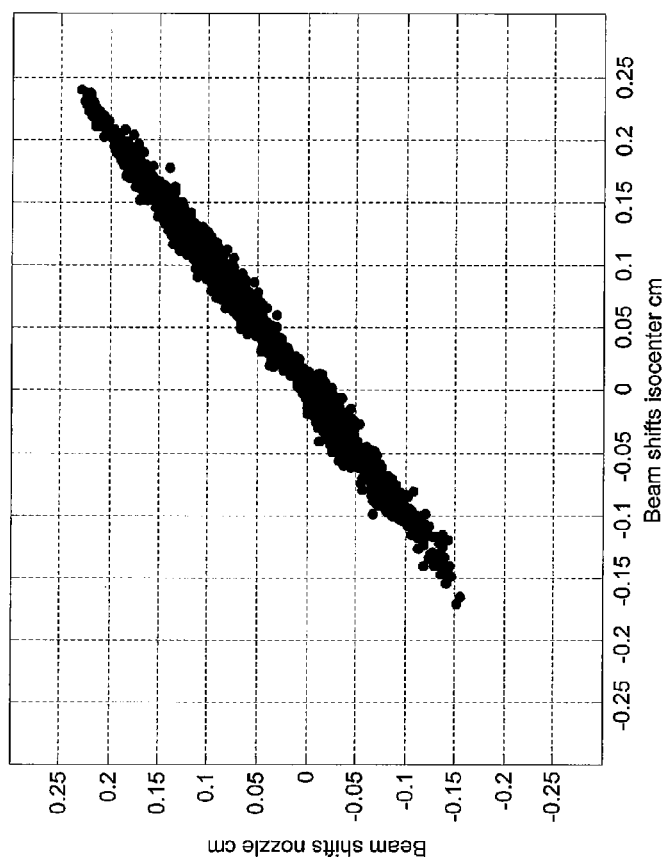
FIG. 9 an 1:1 correlation of the measured beam position shifts at the iso-center and at the nozzle, after applying the corrections of the teaching method to the case shown in FIG. 5; the measured shifts are within the limits given by the precision of the measurement identical.

FIG. 9 show the good correlation between position errors at the iso-center and position errors at the nozzle. The data refer to the case of FIG. 5. This shows that a very good correlation is maintained even for the "wild case" of scanning the energy.

The invention claimed is:

1. A system for delivery of proton therapy by pencil beam scanning of a predeterminable volume within a patient, the system comprising:
  a proton source for generating a proton beam being adjustable with respect to beam intensity, beam energy or the beam intensity and the beam energy;
  a number of proton beam bending and/or focusing units;
  a beam nozzle having an outlet for the proton beam to penetrate the predeterminable volume of the patient;
  a beam bending magnet disposed upstream of said beam nozzle;
  a plurality of sweeper magnets for sweeping the proton beam in both lateral directions;
  a first position-sensitive detector aligned with said beam nozzle for controlling a position of the proton beam;
  a second position-sensitive detector integrated into a patient table;
  control logic for controlling the position and energy of the proton beam and having a beam steering data set; and
  correction logic aligned with said control logic for correcting beam position errors by comparing an expected beam position with an actual beam position detected in said first position-sensitive detector and generating beam position correction data in dependency on comparison results, the beam position correction data is introduced into the beam steering data set after running a patient-field specific steering file to identify scan specific corrections, and wherein said correction logic further uses a generic dynamic correction model for correcting the beam position errors which decay as a function of time after a change of proton energy.

2. The system according to claim 1, wherein said correction logic has automated software for feeding back the beam position correction data derived from comparison data logged from a test irradiation for verification of a therapy-specific beam steering data set into an improved new version of the beam steering data set of the test irradiation which is then qualified to be used for treating the patient in at least one subsequent irradiation.

3. The system according to claim 1, wherein said second position-sensitive detector is disposed in an iso-center of proton beam geometrics.

4. The system according to claim 1, further comprising a degrader for adjusting the proton beam with respect to the beam intensity and the beam energy.

5. A method for improving quality of beam delivery in a system for a delivery of proton therapy by pencil beam scanning of a predeterminable volume within a patient, which comprises the steps of:
  providing a proton source for generating a proton beam being adjustable with respect to a beam intensity, beam energy or the beam intensity and the beam energy;
  providing a number of proton beam bending and/or focusing units for generating a beam line;
  providing a beam nozzle having an outlet for the proton beam to penetrate the predeterminable volume of the patient;
  providing a beam bending magnet disposed upstream of the beam nozzle;
  providing a couple of sweeper magnets for sweeping the proton beam in both lateral directions;
  providing a position-sensitive detector aligned with the beam nozzle for controlling a position of the proton beam;
  integrating a further position-sensitive detector into a patient table;
  providing control logic for controlling the position and energy of the proton beam by using a beam steering data set;
  providing correction logic aligned with the control logic for correcting beam position errors by comparing an expected beam position with an actual beam position detected in the position-sensitive detector; and
  generating beam position correction data in dependency of comparison results, wherein the beam position correction data is introduced into the beam steering data set after running a patient-field specific steering file for identifying scan specific corrections, and wherein the correction logic further uses a generic dynamic correction model for correcting the beam position errors which decay as a function of time after a change of proton energy.

6. The method according to claim 5, wherein the correction logic has automated software for feeding back the beam position correction data derived from comparison data logged from a patient-related test irradiation for verification of an therapy-specific beam steering data set into an improved new version of the beam steering data set of the patient-related test irradiation which is then qualified to be used for treating the patient in at least one subsequent irradiation.

7. The method according to claim 5, which further comprises disposing the further position-sensitive detector in an iso-center of proton beam geometrics.

8. The method according to claim 5, which further comprises providing a degrader for adjusting the proton beam with respect to the beam intensity, the beam energy or the beam intensity and the beam energy.

* * * * *